United States Patent [19]

Otten

[11] Patent Number: 5,344,439
[45] Date of Patent: Sep. 6, 1994

[54] CATHETER WITH RETRACTABLE ANCHOR MECHANISM

[75] Inventor: Lynn M. Otten, Blaine, Minn.

[73] Assignee: Medtronic, Inc., Minneapolis, Minn.

[21] Appl. No.: 969,600

[22] Filed: Oct. 30, 1992

[51] Int. Cl.$^5$ .............................................. A61N 1/05
[52] U.S. Cl. .................................... 607/126; 607/120; 604/105; 604/107
[58] Field of Search ............... 128/642; 607/122, 126, 607/128, 120, 116, 119; 604/105, 106, 107; 606/198

[56] References Cited

U.S. PATENT DOCUMENTS

| | | |
|---|---|---|
| 3,902,501 | 9/1975 | Citron et al. |
| 4,285,347 | 8/1981 | Hess . |
| 4,360,031 | 11/1982 | White .................................. 607/120 |
| 4,419,819 | 12/1983 | Dickhudt et al. . |
| 4,660,571 | 4/1987 | Hess et al. ........................ 607/116 |
| 4,913,164 | 4/1990 | Greene et al. . |
| 4,957,118 | 9/1990 | Eriebacher . |
| 5,156,151 | 10/1992 | Imran .................................. 607/122 |
| 5,179,962 | 1/1993 | Dutcher et al. .................... 607/126 |

Primary Examiner—Lee S. Cohen
Assistant Examiner—Jeffrey R. Jastrzab
Attorney, Agent, or Firm—Harold R. Patton; Terry L. Wiles

[57] ABSTRACT

A catheter with a retractable anchor mechanism for providing drugs and/or electrical stimulation to the human body. The catheter has a flexible tubular casing consisting of a outer member and an inner member which enclose at least one lumen. The retractable anchor mechanism is located near the distal end of the catheter and is moveable from a first extended position to a second retracted position. A capture member is connected to the anchor mechanism. The capture member has a socket portion and a necked down portion for guiding the enlarged tip of a stylet into the socket portion for releasable engagement therewith. The anchor mechanism is moved from the first extended position to the second retracted position by inserting a stylet and applying pressure in the distal direction and is moved from the second retracted position to the first extended position by partially withdrawing the stylet thereby applying pressure in the proximal direction. The anchor mechanism consists of a plurality of lobes in one embodiment and of a continuous diaphragm in another.

12 Claims, 2 Drawing Sheets

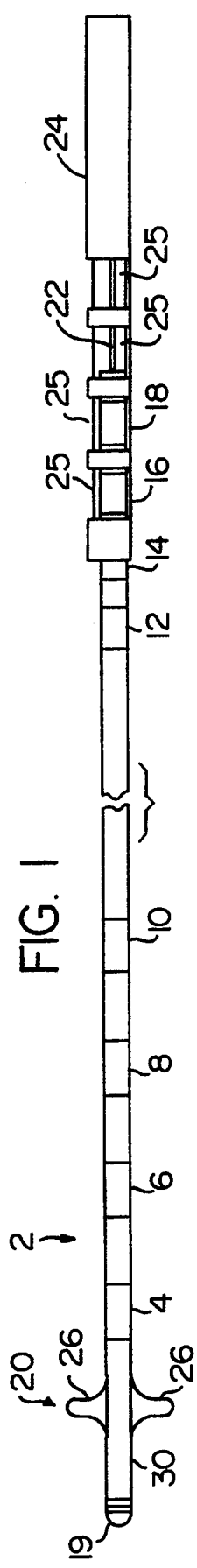
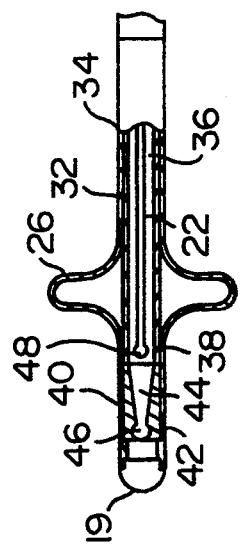
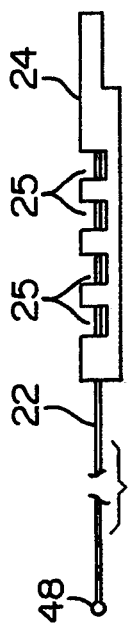
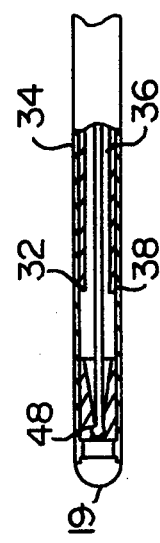

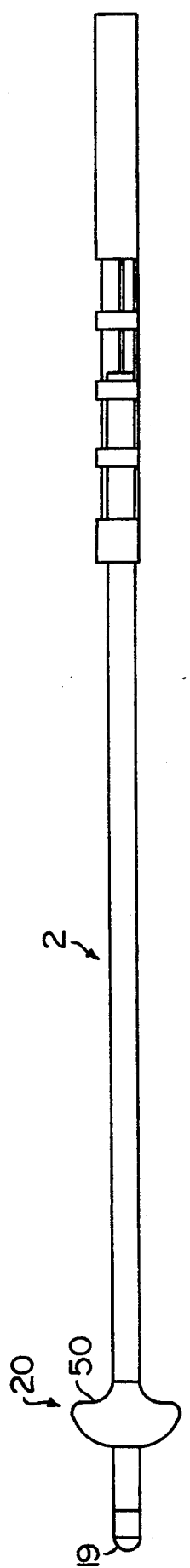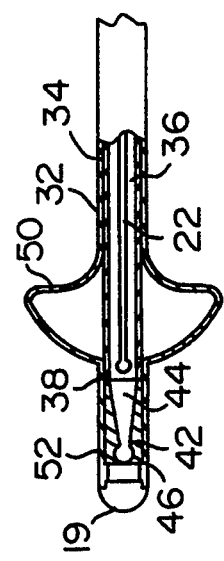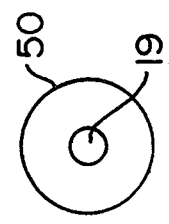

CATHETER WITH RETRACTABLE ANCHOR MECHANISM

Reference is made to our co-pending application, Ser. No., filed on even date herewith entitled LEAD WITH STYLET CAPTURE MEMBER which is hereby incorporated by reference.

FIELD OF THE INVENTION

This invention relates to catheters (which in the context hereof includes those capable of delivery or removal of fluids and/or electrode catheters for delivery of electrical stimulation) having an anchoring mechanism for securing the catheter in the desired location in the human body. More particularly, the invention is directed to a catheter having a releasably engageable stylet for controlling the extension or retraction of the anchor mechanism to provide a reduced cross section at times of introduction and/or repositioning or removal of the catheter and an increased cross section at the time when locational stability of the catheter is desired.

BACKGROUND OF THE INVENTION

The state of the art of implantable pulse generators for stimulating human tissue has advanced to the point that such devices are being designed and used in increasing numbers to treat a wide variety of medical conditions. In addition to implantable pulse generators for treating many different types of cardiac conditions (bradycardia, tachycardia, fibrillation, and the like), so-called neurological pulse generators have been provided for stimulating a patient's nervous system, in order to treat such diverse conditions as pain, motor impairment, incontinence, spasticity, tremor, and impotence, to name only a few.

In most cases, electrical stimulation pulses are conveyed from an implanted pulse generator to the desired stimulation site by means of an implanted lead having exposed electrodes at its distal end. In order to achieve the desired effects from delivery of stimulating pulses it is of course very important that the lead be properly positioned and stabilized in the patient, so that as much of the stimulating energy as possible is delivered to the appropriate site. While this is true for all kinds of stimulation pulse therapies, lead positioning is especially critical in the area of neurological pacing, such as when stimulation pulses are delivered by a lead positioned in the epidural space adjoining the patient's spinal column. Even if the initial lead placement is correct the problem of lead migration often occurs. The delicate and highly sensitive nature of the spinal column, and the possible harmful or otherwise undesirable effects of delivering stimulation pulses to an inappropriate site in this area accentuates the need for precise lead placement and the ability to stabilize or anchor the lead at the appropriate site.

Proper placement is also important in the positioning of catheters used in the injection or withdrawal of fluids from the body. If the proper location cannot be maintained the fluids may be introduced or withdrawn from the wrong location or other problems may be encountered. For example, a recurring problem encountered with catheters introduced into the intrathecal space is catheter migration. If the catheter slips out of the intrathecal space not only is the drug not delivered in the proper location but a leakage of spinal fluid may also occur.

Attempts have been made in the field of neurological stimulation to develop leads which overcome the problem of lead migration. One such lead is disclosed in U.S. Pat. No. 4,285,347 to Hess. Disclosed is an epidural electrode lead having a distal end portion with a resilient portion which is laterally extended when a stylet is not inserted. Insertion of the stylet operates to straighten the resilient portion so that it is no longer laterally extended. The lead is inserted into the spinal canal through a Touhy needle with the stylet inserted. When the distal end of the lead is properly located the stylet is removed and the resilient portion returns to its original laterally extended shape for the purpose of stabilizing the lead.

A biomedical lead utilizing a lobed lead anchor for stability is disclosed in U.S. Pat. No. 4,419,819 to Dickhudt, et al. The lobes are formed utilizing a length of tubing which is slit along a direction parallel to its axis. The tubing is slipped over the lead body and compressed so that the slit portions of the tubing expand into lobes. While the tubing is compressed its ends are fused to the lead body, thus producing a biomedical lead having four curved lobes near its distal end. Again, the lead is inserted through a Touhy needle with a stylet inserted. Pressure in the distal direction on the stylet keeps the lobes retracted until the lead is properly located. Once the stylet is retracted the lobes expand outwardly to their preformed configuration to stabilize the lead.

In the field of cardiac pacing leads the use of an anchoring mechanism for anchoring the distal tip with respect to the inside of the heart is well known and very important to a successful pacing system. A widely used anchoring mechanism is that of tines, as disclosed in U.S. Pat. No. 3,902,501 to Citron, et al. The tined lead provides a plurality of pliant tines that extend from an area adjacent the distal tip of the leads, the tines forming an acute angle with the lead body. The tines are effective in engaging the trabeculae found in the ventricle as well as the atrium, to maintain the electrode tip in a secure position after the physician has positioned it for good pacing threshold. Other variations of the tined lead concept are disclosed in U.S. Pat. Nos. 4,913,164 to Greene et al., 4,957,118, to Erlebacher, and in German Patent Application 33 00 050.

The problem with these devices is that either they allow the physician only limited control over the anchoring mechanism when they are being inserted or they are very complicated both in terms of construction and use. In most the physician must rely on the "memory" of the tines, lobes or other anchoring configuration to secure the lead once the stylet is removed. Although some leads such as those disclosed in U.S. Pat. Nos. 4,913,164 and 4,957,118 provide the physician with control over both extension and retraction of the tines, the mechanisms rely on a complex strut system which is both difficult to operate and to manufacture. Additionally, once the leads are implanted for any length of time tissue ingrowth would make the tines difficult to retract.

In order to overcome the problems associated with present anchoring mechanisms it can thus be seen that there is a need for a lead having an easy to use anchoring mechanism which provides the physician with control over both extension and retraction of the mechanism while at the same time eliminating the complex structure associated with present leads.

SUMMARY OF THE INVENTION

In accordance with the present invention there is disclosed an improved catheter having a retractable anchor mechanism. In one embodiment the catheter is used to deliver drugs or other fluids to the body. In another, the invention is an electrode catheter used to deliver electrical stimulation to body tissue such as an epidural lead.

Disclosed is a catheter having a distal end and a proximal end for insertion in the human body. The catheter has a flexible tubular outer casing which is substantially concentric to the longitudinal axis of the catheter and defines at least one lumen. The outer casing may consist of an outer tubular member extending generally between the distal and proximal ends of the catheter and an inner tubular member extending substantially from the proximal end to a position near the distal end. A retractable anchor means is located near the distal end to stabilize the catheter within the body. The anchor means is moveable from a first extended position to a second retracted position. In one embodiment the anchor means comprises a formed portion of the outer member which has an outer dimension substantially identical to the outer dimension of the remainder of the outer member when it is in the second retracted position and which has an outer dimension greater than the outer dimension of the remainder of the outer member when in the first expended position. In another embodiment the anchor means comprises a plurality of longitudinal slits formed in the outer member which define a plurality of lobes. The lobes are compressed and extend outwardly away from the longitudinal axis of the catheter when in the first extended position and lie substantially parallel to the longitudinal axis of the catheter when in the second retracted position. A stylet having an enlarged tip of predetermined shape at the distal end is provided for insertion in the central lumen. The stylet is releasably received in a capture means which is connected to the anchor means. The capture means has an aperture which is shaped to accommodate the predetermined shape of the distal end of the stylet.

By inserting the stylet and applying pressure in the distal direction the anchor means is moved from the first extended position to the second retracted position and the enlarged distal end of the stylet is captured by the capture means. Partially withdrawing the stylet by applying pressure in the proximal direction results in the anchor means moving to the first extended position. The movement of the capture means is limited by contact with the distal end of the inner member so that further pressure in the proximal direction results in release of the enlarged distal end of the stylet by the capture means.

In one embodiment the catheter is an electrode catheter and has at least one electrode located near the distal end and at least one conductor for transmitting electrical signals from the proximal end of the catheter to the electrode. In another embodiment the catheter includes at least one port between at least one lumen and the exterior of the catheter for introduction or withdrawal of fluids.

BRIEF DESCRIPTION OF THE DRAWINGS

The foregoing and other aspects of the present invention will be best appreciated with reference to the detailed description of the invention, which follows, when read in conjunction with the accompanying drawings wherein:

FIG. 1 is an illustration of an electrode catheter with a retractable anchor mechanism in the first extended position in accordance with one embodiment of the present invention;

FIG. 2 is a side view of the distal end of the catheter of FIG. 1 showing the anchor mechanism in the second retracted position;

FIG. 3 is an end view of the catheter of FIG. 1;

FIG. 4 is a partially cut-away side view of the distal end of the catheter of FIG. 1;

FIG. 5 is a partially cut-away side view of the distal end of the catheter of FIG. 1 with the anchor mechanism in the second retracted position;

FIG. 6 is an illustration of the stylet in accordance with the present invention;

FIG. 7 is an illustration of a catheter with a retractable anchor mechanism in the first extended position in accordance with another embodiment of the present invention;

FIG. 8 is an end view of the catheter of FIG. 7;

FIG. 9 is a partially cut-away side view of the distal end of the catheter of FIG. 7;

FIG. 10 is a partially cut-away side view of the distal end of the catheter of FIG. 7 with the anchor mechanism in the second retracted position.

DETAILED DESCRIPTION OF THE INVENTION

In FIGS. 1 through 5 there is shown an electrode catheter 2 in accordance with one embodiment of the present invention. Catheter 2 is provided with one or more electrodes 4, 6, 8 and 10 which are connected by conductors (not shown) in a conventional manner to contacts 12, 14, 16 and 18 located at the proximal end of catheter 2. Near the distal end 19 of catheter 2 is an anchor mechanism 20 which is shown in a first extended position in FIGS. 1, 3 and 4 and in a second retracted position in FIGS. 2 and 5. Electrode catheter 2 may be an epidural stimulating lead and may be constructed similar to neurological stimulation leads marketed by Medtronic, Inc. and identified as Model Nos. 3885, 3888, 3487T or 3487A with the addition of anchor mechanism 20.

With reference to FIG. 1, which is an illustration of catheter 2 with a retractable anchor mechanism in the extended position, a stylet 22 is shown partially inserted in catheter 2. Stylet 22 is connected to stylet handle 24 as shown in FIG. 6. Stylet handle 24 is provided with a plurality of openings 25 which are positioned such that when stylet 22 is fully inserted into catheter 2 contacts 12, 14, 16 and 18 are exposed through openings 25. This allows contacts 12, 14, 16 and 18 to be temporarily connected to an external stimulator such as, for example, a Medtronic Model 3625 Neurological Screener while the stylet is inserted. After the optimum placement of the catheter is determined the stylet is removed and the catheter is connected to an implanted receiver or pulse generator for long term nerve or muscle stimulation.

With continued reference to FIG. 1, anchor mechanism 20 consists, in this embodiment, of a plurality of lobes 26. Lobes 26 are formed by a plurality of longitudinal slits 28 in the flexible tubular outer casing 30 of catheter 2 as shown in FIG. 2. Tubular outer casing 30 may be of polyurethane, silicone rubber or other biologically compatible polymer and may be of one piece construction or may consist of an outer tubular member 32 and an inner tubular member 34, as shown in FIGS. 4 and 5. The inner surface of inner tubular member 34 defines a central lumen 36 through which stylet 22 is inserted. Although a total of four lobes 26 are illustrated in this embodiment and that number has been found to be particularly advantageous a greater or lesser number of lobes could be utilized within the scope of this invention.

The movement of lobes 26 from the first extended position to the second retracted position or vice versa may be explained with reference to FIGS. 4 and 5 which are partially cut-away side views of the catheter of FIG. 1 with the anchor mechanism in the extended position and with the anchor mechanism in the retracted position, respectively. Lobes 26 are heat formed so that the flexible material from which they are made tends to remain in the first extended position in the absence of external force being applied. Thus, with stylet 22 only partially inserted as in FIGS. 1 and 4, lobes 26 are in the extended position. In this position the distal end 38 of inner tubular member 34 butts against a capture member 40, acting as a stop. Capture member 40 is positioned near the distal end of the catheter and is secured to the inner surface of outer tubular member 32. Capture member 40 includes an aperture 42 having a necked down portion 44 and a socket portion 46. Socket portion 46 is shaped to accommodate an enlarged tip 48 of predetermined shape on the distal end of stylet 22.

As stylet 22 is advanced towards distal end 19, enlarged tip 48 enters necked down portion 44 and is guided towards socket portion 46. As lobes 26 reach their retracted position the enlarged tip 48 of stylet 22 is urged into socket portion 46. In addition to directing the enlarged tip of the stylet into the socket portion, necked down portion 44 also protects the catheter from potential stylet puncture even in situations where the catheter is bent. A further advantage of this construction is that the physician tactilely feels the engagement and disengagement when enlarged tip 48 pops into and out of socket portion 46. Thus, the physician can "feel" when the anchor mechanism is expanded or retracted. FIG. 5 illustrates catheter 2 with lobes 26 fully retracted and with enlarged tip 48 releasably received within socket portion 46.

Once enlarged tip 48 is received within socket portion 46, lobes 26 may be extended or retracted any number of times by the physician as the catheter is positioned. When the optimum placement has been determined and the catheter is placed at the desired location the lobes are extended by withdrawing stylet 22. It is important to note that the physician is able to directly control both retraction and extension of the anchor mechanism. By inserting the stylet and applying pressure in the distal direction the anchor mechanism is retracted. Likewise, once enlarged tip 48 has been received by socket portion 46, a partial withdrawal of the stylet applies pressure in the proximal direction on the anchor mechanism causing extension of the anchor mechanism. Therefore, the physician is able to affirmatively extend and set the lobes and does not have to rely on the "memory" of the heat formed lobes to extend and set themselves. This is significant since in many applications there is not enough room for the lobes to expand fully. In these situations the effectiveness of the anchor mechanism is enhanced by being able to apply external pressure to force the lobes into the surrounding tissue.

Lobes 26 are fully extended when stylet 22 has been withdrawn to the extent that capture member 42 butts against distal end 38 of inner tubular member 34. When in this position further pressure in the proximal direction by continued withdrawal of stylet 22 results in release of enlarged tip 48 from socket portion 46 allowing complete withdrawal of stylet 22. As mentioned previously, an advantage of this construction is that the physician is able to tactiley feel the disengagement of enlarged tip 48 from socket portion 46. The physician is thus assured that the anchor mechanism is fully extended and may proceed to remove the stylet.

The improved anchor mechanism of the present invention is also advantageous if the catheter must at some future time be removed or repositioned. If that is necessary a stylet may be reinserted in the catheter and advanced in the manner described earlier in order to retract the anchor mechanism. When the physician "feels" the engagement of enlarged tip 48 with socket portion 46 the physician knows that the anchor mechanism has been retracted. The catheter is then ready to be removed or repositioned. If the catheter is to be repositioned, once the new location is determined and the catheter moved, the anchor mechanism can be expanded as previously described and the stylet once again removed.

FIGS. 7 through 10 illustrate a further embodiment of the present invention, wherein like reference numerals indicate like parts as above. FIG. 7 is an illustration of a catheter 2 with a retractable anchor mechanism 20 in the first extended position. In this embodiment anchor mechanism 20 consists of a heat formed portion of outer tubular member 32 located near distal end 19. The heat forming process results in anchor mechanism 20 taking the form of a continuous circular diaphragm 50. Circular diaphragm 50 may be supported by splines or ribs for additional structural support if desired. The heat forming process causes diaphragm 50 to remain in the extended position in the absence of external forces being applied. FIGS. 7, 8 and 9 show catheter 2 with diaphragm 50 in the extended position. As clearly shown in FIG. 8, the outer dimension of diaphragm 50 is greater than the outer dimension of outer tubular member 32 when in the extended position. FIG. 10 shows catheter 2 with diaphragm 50 in the retracted position. When in the retracted position the outer dimension of diaphragm 50 is substantially identical to the outer dimension of outer tubular member 32.

With reference to FIG. 9, which is a partially cut-away side view of the distal end of catheter 2, capture member 42 is provided with one or more ports 52 which provide a path for fluids to travel between central lumen 36 and the exterior of catheter 2. Although shown in this position, ports 52 may be positioned at any location on the distal side of diaphragm 50. Additionally, although catheter 2 is shown having a single central lumen it could be constructed with two or more separate lumens, each connected to the exterior by one or more ports 52. In this manner it would be possible to infuse or withdraw two or more fluids at the same time.

The extension and retraction of diaphragm 50 is accomplished in the same manner as described above with respect to the lobed anchor mechanism. With reference to FIGS. 9 and 10, when stylet 22 is advanced towards distal end 19, enlarged tip 48 enters necked down portion 44 and is directed towards socket portion 46. When diaphragm 50 reaches its retracted position the enlarged tip 48 of stylet 22 is urged into socket portion 46 temporarily locking enlarged tip 48 in capture member 42. The catheter can then be positioned in the desired location at which time stylet 22 is withdrawn causing the extension of diaphragm 50.

This embodiment is particularly advantageous for use in drug delivery catheters such as the Medtronic Model Nos. 8703 and 8700 a or b. Such catheters are often inserted in the intrathecal space for delivery of drugs used in treatment of chronic pain, spasticity and the like. A typical problem encountered is migration of the catheter out of the intrathecal space. Even if the catheter does not migrate there may be a problem with spinal fluid leaking out around the catheter at the point of insertion in the intrathecal space. These problems may be solved by equipping the catheter with a diaphragm anchor mechanism in accordance with this embodiment. The catheter is inserted far enough so that the retracted diaphragm is within the intrathecal space. The diaphragm is then expanded so that the catheter is anchored in the intrathecal space. When so expanded, the diaphragm acts as a "plug" to diminish the extent of any leakage of spinal fluid around the catheter. The unique construction of the anchor mechanism allows the diaphragm to be retracted at a later time if the catheter is to be removed. This is easily accomplished be reinserting a stylet into the catheter and advancing it to retract the diaphragm in the manner previously described.

From the foregoing detailed description of specific embodiments of the invention, it should be apparent that a catheter with a retractable anchor mechanism has been disclosed. Although two particular embodiments of the invention have been disclosed herein in detail, this has been done for the purpose of illustration only, and is not intended to be limiting with respect to the scope of the appended claims, which follow. In particular, it is contemplated by the inventors that various substitutions, alterations and modifications may be made to the embodiments of the invention described herein without departing from the spirit and scope of the invention as defined by the claims. For instance, the choice of materials or variations of the shape of the anchor mechanism, the socket portion or the distal tip of the stylet are believed to be a matter of routine for a person of ordinary skill in the art with knowledge of the embodiments disclosed herein. Likewise, although the embodiments disclosed relate primarily to spinal cord stimulation and/or drug delivery, the anchor mechanism could be used for other applications such as cardiac pacing leads or other portions of the body where a stabilization method is required.

I claim:

1. An elongated catheter having a distal end and a proximal end, the distal end of which is adapted to be inserted into a human body, the catheter comprising:
    a flexible tubular casing substantially concentric to a longitudinal axis of the catheter, said casing extending substantially the entire length of the catheter and defining at least one lumen,
    retractable anchor means located near the distal end for stabilizing the position of the catheter within the body, said anchor means comprising a portion of said flexible tubular casing and being moveable from a first extended position to a second retracted position,
    a stylet for insertion in said at least one lumen of the catheter, said stylet having an enlarged tip of predetermined shaped at a distal end, there of and
    capture means connected to said anchor means for releasably receiving the enlarged tip of said stylet, such that said anchor means is moved from the first extended position to the second retracted position by inserting said stylet and applying pressure in a distal direction and is moved from the second retracted position to the first extended position by applying pressure in a proximal direction.

2. The catheter of claim 1 further including at least one electrode located in the casing near the distal end of the catheter and at least one conductor within the casing and connected to the at least one electrode for transmitting electrical signals from the proximal end of the catheter to said at least one electrode.

3. The catheter of claim 1 further including at least one port in the casing between said at least one lumen and an exterior of the catheter, said at least one port being located between the distal end of the catheter and said retractable anchor means, such that drugs or other therapeutic agents may be introduced into the body or body fluids may be withdrawn from the body through said at least one port.

4. The catheter of claim 2 or 3 wherein said tubular casing comprises an outer tubular member extending between the distal and proximal ends of the catheter and an inner tubular member extending substantially from the proximal end of the catheter to a position near the distal end, said inner tubular member having a distal end which contacts said capture means when said retractable anchor means is in the first extended position, such that continued pressure on said stylet in the proximal direction results in release of the distal end of said stylet from said capture means.

5. The catheter or claim 1 wherein said capture means comprises a capture member including an aperture having a necked down portion and a socket portion, said socket portion being shaped to accommodate the predetermined shape of the enlarged tip of said stylet.

6. An elongated catheter having a distal end and a proximal end, the distal end of which is adapted to be inserted into a human body, the catheter comprising:
    a flexible tubular outer member substantially concentric to a longitudinal axis of the catheter, said outer member extending substantially the entire length of the catheter;
    a flexible tubular inner member lying within said outer member, said inner member having a distal end located near the distal end of the catheter, said inner member extending substantially to the proximal end of the catheter and defining a central lumen,
    retractable anchor means located near the distal end of the catheter for stabilizing the position of the catheter within the body, said anchor means comprising a portion of said flexible tubular outer member and being moveable from a first extended position to a second retracted position,
    at least one port in the outer member between the central lumen and an exterior of the catheter, said at least one port being located between the distal end of the catheter and said retractable anchor means, such that drugs or therapeutic agents may be introduced into the body or body fluids may be withdrawn from the body through said at least one port,
    a stylet for insertion in the central lumen of the catheter, said stylet having an enlarged tip of predetermined shape at a distal end, thereof and capture means connected to said anchor means for releasably receiving the enlarged tip of said stylet, the movement of said capture means being limited in a proximal direction by the distal end of said inner member which acts as a stop, such that said anchor means is moved from the first extended position to the second retracted position by inserting said stylet and applying pressure in a distal direction and is moved from the second retracted position to the first extended position by applying pressure in the proximal direction until said capture means contacts the distal end of said inner member at which point continued pressure in the proximal direction results in release of the enlarged tip of said stylet from said capture means.

7. The catheter or claim 6 wherein said capture means comprises a capture member including an aperture having a necked down portion and a socket portion, said socket portion being shaped to accommodate the predetermined shape of the enlarged tip of said stylet.

8. The catheter of claim 6 further comprising at least one additional lumen, said at least one additional lumen having a path to the exterior of the catheter provided by said at least one port, such that one or more drug, agents or fluids may be introduced or withdrawn at the same time.

9. An epidural lead having a distal end and a proximal end, the distal end of which is adapted to be inserted into a human body, the epidural lead comprising:
a flexible tubular outer member substantially concentric to a longitudinal axis of the lead, said outer member extending substantially the entire length of the lead,
a flexible tubular inner member lying within said outer member, said inner member having a distal end located near the distal end of the lead, said inner member extending substantially to the proximal end of the lead and defining a central lumen,
at least one electrode secured to said outer member near the distal end of the lead,
at least one conductor connected to said at least one electrode for transmitting electrical signals from the proximal end of the lead to said a least one electrode,
retractable anchor means located near the distal end of the lead for stabilizing the position of the lead within the body, said anchor means comprising a portion of said flexible tubular outer member and being moveable from a first extended position to a second retracted position,
a stylet for insertion in the central lumen of the lead, said stylet having an enlarged tip at a distal end, thereof and
capture means connected to said anchor means for releasably receiving the enlarged tip of said stylet, the movement of said capture means being limited in a proximal direction by the distal end of said inner member which acts as a stop, such that said anchor means is moved from the first extended position to the second retracted position by inserting aid stylet and applying pressure in the proximal direction until said capture means contacts the distal end of said inner member at which point continued pressure in the proximal direction results in release of the enlarged tip of said stylet from said capture means.

10. The epidural lead of claim 9 wherein said capture means comprises a capture member including an aperture having a necked down portion and a socket portion, said socket portion being shaped to accommodate the predetermined shape of the enlarged tip of said stylet.

11. An elongated catheter having a distal end and a proximal end, the distal end of which is adapted to be inserted into a human body, the catheter comprising:
a flexible tubular outer member substantially concentric to a longitudinal axis of the catheter, said outer member extending substantially the entire length of the catheter,
a flexible tubular inner member lying within said outer member, said inner member having a distal end located near the distal end of the catheter, said inner member extending substantially to the proximal end of the catheter and defining a central lumen,
retractable anchor means located near the distal end of the catheter for stabilizing the position of the catheter within the body, said anchor means being movable from a first extending position to a second retracted position, said retractable anchor means comprising a formed portion of said outer member, sad formed portion having an outer dimension substantially identical to an outer dimension of the remainder of the outer member when in the second retracted position and having an outer dimension greater than the outer dimension of the remainder of the outer member when in the first extended position,
at least one port int eh outer member between the central lumen and an exterior of the catheter, said at least one port being located between the distal end of the catheter and said retractable anchor means, such that drugs or therapeutic agents may be introduced into the body or body fluids may be withdrawn from the body through said at least one port,
a stylet for insertion in the central lumen of the catheter, said stylet having an enlarged tip of predetermined shape at a distal end, thereof and
capture means connected to said anchor means for releasably receiving the enlarged tip of said stylet, the movement of said capture means being limited in a proximal direction by the distal end of said inner member which acts as a stop, such that said anchor means is moved from the first extended position to the second retracted position by inserting said stylet and applying pressure in a distal direction and is moved from the second retracted position to the first extended position by applying pressure in the proximal direction until said capture means contacts the distal end of said inner member at which point continued pressure in the proximal direction results in release of the enlarged tip of said stylet from said capture means.

12. An epidural lead having a distal end and a proximal end, the distal end of which is adapted to be inserted into a human body, the epidural lead comprising:
a flexible tubular outer member substantially concentric to a longitudinal axis of the lead, said outer member extending substantially the entire length of the lead,
a flexible tubular inner member lying within said outer member, said inner member having a distal end located near the distal end of the lead, said inner member extending substantially to the proximal end of the lead and defining a central lumen, at least one electrode secured to said outer member near the distal end of the lead, at least one conductor connected to said at least on electrode for transmitting electrical signals from the proximal end of the lead to said a least one electrode, retractable anchor means located near the distal end of the lead for stabilizing the position of the lead within the body, said anchor means being moveable from a first extended position to a second retracted position, said retractable anchor mans comprising a plurality of longitudinal slits formed in said outer member, said slits defining a plurality of lobes which are compressed and extend outwardly away from the longitudinal axis of the lead when in the first extended position and which lie substantially parallel to the longitudinal axis access of the lead when in the second retracted position, a stylet for insertion in the central lumen of the lead, said stylet having an enlarged tip at a distal end thereof, and capture means connected to said anchor means for releasably receiving the enlarged tip of said stylet, the movement of said capture means being limited in a proximal direction by the distal end of said inner member which acts as a stop, such that said anchor means is moved from the first extended position to the second retracted position by inserting said stylet and applying pressure in the proximal direction until said capture means contacts the distal end of said inner member at which point continued pressure in the proximal direction results in release of the enlarged tip of said stylet from said capture means.

* * * * *